Nov. 21, 1950 R. I. McLELLAN ET AL Plant Pat. 989
GARDENIA PLANT
Filed July 2, 1949
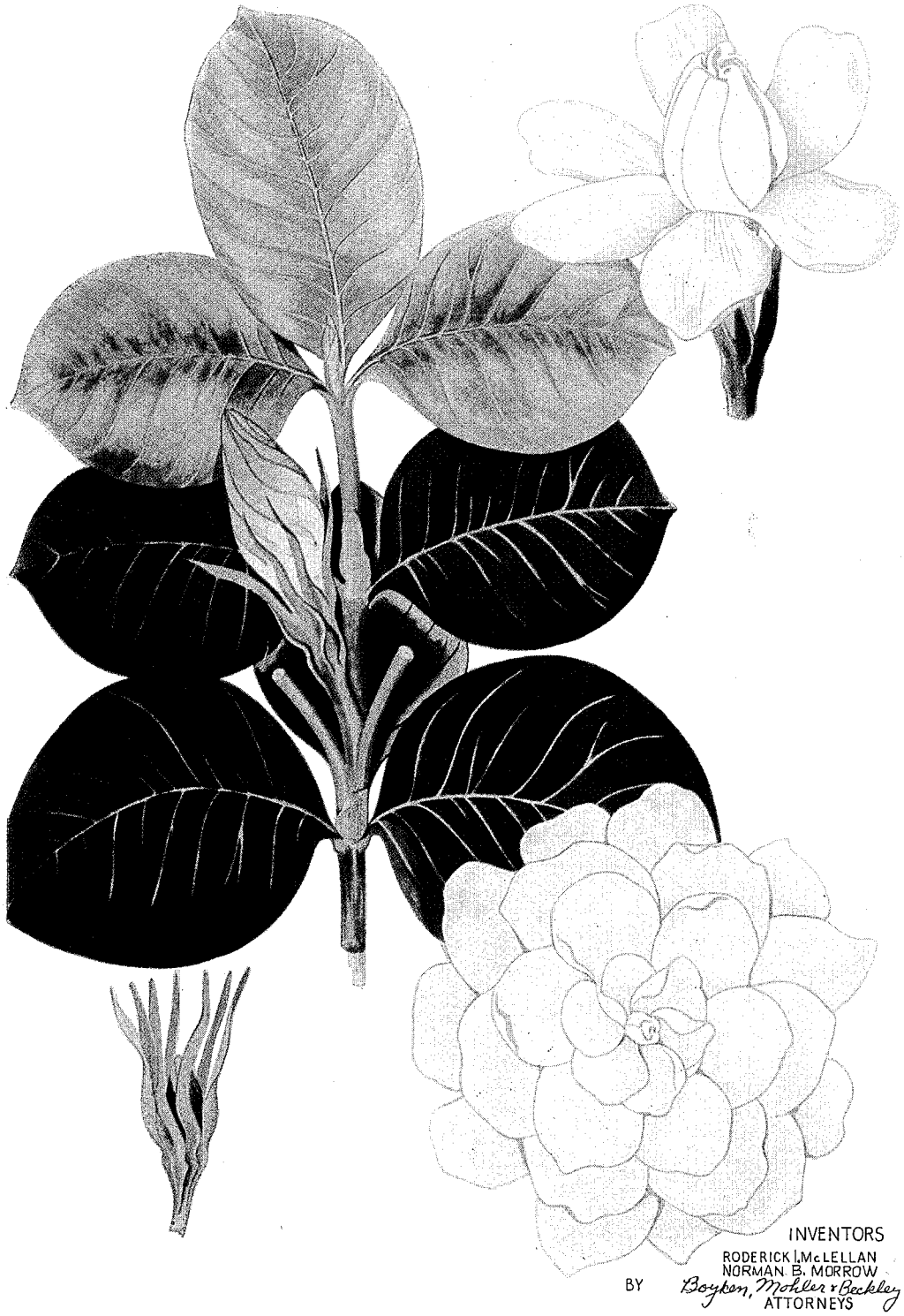
INVENTORS
RODERICK I. McLELLAN
NORMAN B. MORROW
BY Boyken, Mohler & Beckley
ATTORNEYS Patented Nov. 21, 1950 Plant Pat. 989

UNITED STATES PATENT OFFICE

989

GARDENIA PLANT

Roderick I. McLellan, Hillsborough, and Norman B. Morrow, San Bruno, Calif., assignors to E. W. McLellan Company, Colma, Calif., a corporation of California Application July 2, 1949, Serial No. 102,886

1 Claim. (Cl. 47—60)

This invention relates to improvements in gardenia plants of the general type grow in greenhouses in various parts of the United States, and the object of the invention is to provide a new and distinct variety of gardenia plant having many desirable and useful qualities not previously existing in any known single variety, some of which are; more, thicker, and broader petals; stronger and heavier corolla, calyx, nodes, internodes, roots; a more compact and stiffer plant; leaves that are wider and thicker; a tetraploid, i. e. a strain of a species having double the normal number of chromosomes. Other desirable points wherein the present invention differs from those heretofore known, will appear in the description.

This new variety is a sport or vegetative variation from the *Gardenia jasminoides* var. grandiflora.

Asexual propagation of the newly discovered plant was made at Colma, California, by taking cuttings in the years 1948 and 1949, taking two mature nodes to each cutting and placing the one and one half inch of cutting in a sand rooting medium with bottom heat. The improved qualities of the new variety, as herein described have consistently reproduced, and while the new variety has not as yet been named, it is well established.

The accompanying illustrations show a portion of a stalk and foliage including a well matured bud; a newly formed bud; a partially opened blossom; and a fully opened blossom. The newly formed bud, partially opened flower and fully opened flower are shown separate from the foliage and stalk in order to adequately illustrate each in a large scale, although the same scale is used for all views.

The following is a detailed description of the new gardenia plant and the buds and flowers produced by the same.

As above noted, the parentage of the plant illustrated is "*Gardenia jasmoinoides* var. grandiflora," said plant being a sport or vegetative variation therefrom.

The plants are non-glabrous, leaves opposite in 3's with ovate interpetiolar stipules. Leaves entire, ovate, obtuse with shortened petiole. The mature leaves are dark green and glossy.

The young plants form buds and commence to flower as soon as they are rooted, given the proper temperatures. There is no undeveloped condition.

The corolla tube is slaver shaped and does not exceed the calyx. There are six or seven linear acuminate calyx bracts, green in color and slightly longer than the corolla tube.

The color of the bloom is white, turning yellow with age at the end of from two to six days depending upon the time of the year and heat. Flowers are solitary with ovary inferior, and five rows or more of petals with six to seven petals in each row.

The petals are from two to three inches in length and from one to two inches wide depending upon the time of the year and the size of the flower. The successive inner rows of petals are smaller. The petals are ovate and obtuse, and open to a plane perpendicular to the axis of the corolla, being somewhat incurved when first opening and somewhat recurved when fully opened. The petals never drop from the flower.

The diameters or overall measurements of the flowers are from two to six and one half inches.

The stamens are from three to nine in number and abortive, having become mostly petalized, and frequently semipetaled. The stigma is also abortive due to the compactness and solidness of the center of the multipetaled flower.

The principal differences between the new variety and the grandiflora from which it originated are as follows:

The flower petals are thicker and broader and the flowers average one extra row of petals. Also, there is less recurving to the petals.

The corolla is much heavier and is usually longer, and the calyx is heavier, coarser and thicker.

The nodes are heavier and the internodes are shorter and thicker, being about one third shorter and one third thicker. With the shorter internodes the plant is shorter.

The leaves are of the same length, but are about one third wider and one third thicker, giving the appearance of being much rounder.

The whole plant is stiffer and flops less and the plant growth is more upright and more compact. The plant appears to set buds more readily.

Because of the heavier and thicker petals, there are fewer small flowers than on the regular grandiflora, and the fragrance of the flowers is similar to the grandiflora, but sweeter.

The roots are heavier and coarser.

The new gardenia of this invention is a tetraploid. A tetraploid is a strain of a species that has double the normal number of chromosomes. The chromosome count of all gardenias on record is twenty-two (22), while the chromosome count of the present new variety herein described is forty-four (44). Because of its being a tetraploid, the flower has a velvety texture; there is a heavier texture to the leaves; shorter internodes; thicker stems; more upright growth; and more vigorous root action. The leaves are flatter than the ordinary gardenia leaves, and the margins do not undulate as much.

We claim:

A variety of gardenia plant substantially as shown and described characterized particularly by its being a tetraploid having as distinguishing characteristics relative to the grandiflora variety; broader, heavier and flatter leaves; shorter and thicker internodes and heavier nodes; a greater proportion of exceptionally large, perfect flowers; more petals and an extra row of petals in the average flowers and which petals are broader and thicker; heavier corollas and calyxes with the latter being coarser and thicker; a more compact and stiffer plant as a whole having thicker stems and roots that are heavier and coarser.

RODERICK I. McLELLAN.
NORMAN B. MORROW.

No references cited.